(12) United States Patent
Oguma et al.

(10) Patent No.: US 6,916,938 B2
(45) Date of Patent: Jul. 12, 2005

(54) METHOD FOR PREPARING SULFONE OR SULFOXIDE COMPOUND

(75) Inventors: Jun Oguma, Abiko (JP); Koji Hagiya, Ibaraki (JP); Takashi Miyawaki, Ibaraki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 109 days.

(21) Appl. No.: 10/349,105

(22) Filed: Jan. 23, 2003

(65) Prior Publication Data

US 2003/0171589 A1 Sep. 11, 2003

(30) Foreign Application Priority Data

Feb. 7, 2002 (JP) ........................................ 2002-030736

(51) Int. Cl.[7] ...................... C07D 333/74; C07D 333/48
(52) U.S. Cl. ............................ 549/43; 549/46; 549/83; 549/87
(58) Field of Search ............................. 549/43, 46, 83, 549/87

(56) References Cited

U.S. PATENT DOCUMENTS

| | | | |
|---|---|---|---|
| 4,089,904 A | * | 5/1978 | Cisney et al. .................. 568/33 |
| 5,281,740 A | | 1/1994 | Meier et al. |
| 5,621,097 A | * | 4/1997 | Brown et al. ............... 540/342 |
| 6,040,455 A | | 3/2000 | Wood et al. |

FOREIGN PATENT DOCUMENTS

| | | |
|---|---|---|
| EP | 0 710 647 A1 | 5/1996 |
| EP | 0 323 846 A2 | 7/1998 |
| EP | 1 188 735 A1 | 3/2002 |
| ES | 2 036 948 A1 | 6/1993 |
| ES | 2 060 541 A1 | 11/1994 |
| ES | 2 105 953 A1 | 10/1997 |

OTHER PUBLICATIONS

K. Sato et al., "Oxidation of sulfides to sulfoxides and sulfones with 30% hydrogen peroxide under organic solvent– and halogen–free conditions", Tetrahedron, Elsevier Science Publishers, vol. 57, No. 13, Mar. 26, 2001, pp. 2469–2476.

M. Madesclaire, "Synthesis of Sulfoxides by Oxidation of Thiothers", Tetrahedron, Elsevier Science Publishers, vol. 42, No. 20, (1998), pp. 5459–5495.

H. Schultz et al., "New Catalysts for the Oxidation of Sulfides to Sulfones with Hydrogen Peroxide", Journal of Organic Chemistry, American Chemical Society, vol. 28, Apr. 1963, pp. 1140–1143.

Y. Ishii et al., Selectivity in Oxidation of Sulfides with Hydrogen Peroxide by $[\pi\text{-}C_5H_5N+(CH_2)_{15}CH_3]_3PM_{12}O_{40}{}^{3-}$ and $[\pi\text{-}C_5H_5N+(CH_2)_{15}CH_3]_3\{PO_4[M(O)(O_2)_2]_4\}^{3-}$ (M= Mo or W), Chemistry Letters, 1994, pp. 1–4.

S. Yamazaki, "Selective Synthesis of Sulfoxides and Sulfones by Methyltrioxorhenium–Catalyzed Oxidation of Sulfides with Hydrogen Peroxide", Bull. Chem. Soc. Jpn., vol. 69, 1996, pp. 2955–2959.

W. Adam et al., "Chemoselective Methyltrioxorhenium (VII)–Catalyzed Sulfoxidations with Hydrogen Peroxide", Tetrahedron, vol. 50, No. 46, 1994, pp. 13121–13124.

F.M. Collins et al., "Oxidative desulphurisation of oils via hydrogen peroxide and heteropolyanion catalysis", Jounral of Molecular Catalysis A: Chemical, vol. 117, 1997, pp. 397–403.

N.M. Gresley et al., "Studies on polyoxo and polyperoxo–metalates part 5[1]: Peroxide–catalysed oxidations with heteropolyperoxo–tungstates and –molybdates", Journal of Molecular Catalysis A: Chemical, vol. 117, 1997, pp. 185–198.

O. Bortolini et al., "Metal Catalysis in Oxidation by Peroxides.[1] Sulfide Oxidation and Olefin Epoxidation by Dilute Hydrogen Peroxide Catalyzed by Molybdenum and Tungsten Derivatives under Phase–Transfer Conditions", J. Org. Chem., vol. 50, 1985, pp. 2688–2690.

* cited by examiner

Primary Examiner—Deborah C. Lambkin
(74) Attorney, Agent, or Firm—Sughrue Mion, PLLC

(57) ABSTRACT

There is provided a method for preparing a sulfone or sulfoxide compound, characterized in that a sulfide compound is allowed to react with hydrogen peroxide in the presence of a metal oxide catalyst formed by the reaction of hydrogen peroxide with at least one metal or metal compound selected from tungsten metal; molybdenum metal; a tungsten compound comprising tungsten and a Group IIIb, IVb, Vb, or VIb element exclusive of oxygen; and a molybdenum compound comprising molybdenum and a Group IIIb, IVb, Vb, or VIb element exclusive of oxygen.

10 Claims, No Drawings

METHOD FOR PREPARING SULFONE OR SULFOXIDE COMPOUND

BACKGROUND OF THE INVENTION

1. Field of the Invention

The present invention relates to a method for preparing a sulfone or sulfoxide compound and a catalyst for use therein.

2. Background of the Invention

Sulfone or sulfoxide compounds are important for the production of chemical products and intermediates thereof.

There have been reported processes of preparing sulfone or sulfoxide compounds by the reaction of hydrogen peroxide with sulfide compounds.

For example, J. Org. Chem., 28, 1140 (1963) discloses a process of preparing 2-phenylsulfonylethanol by the reaction of 2-phenylmercaptoethanol with hydrogen peroxide in the presence of a sodium tungstate. However, said method was not effective for other less reactive sulfide other than 2-phenylmercaptoethanol, which is rather reactive sulfide. There have been also reported (1) a process using a cetylpyridinium tungstophosphoric acid as a catalyst (Chem. Lett., 1 (1994)), (2) a process using a methylirheniumtrioxide catalyst (Bull. Chem. Soc. Jpn., 69, 2955 (1996)), (3) a process using quaternary ammonium hydrogensulfate and phenylphosphonic acid in addition to the sodium tungstate (Tetrahedoron, 57, 2469 (2001)). However, these processes are not always industrially satisfactory in that the first process (1) required complicated operations for preparing the catalyst, the catalyst for the second process (2) is expensive, and the third process (3) required expensive phenylphosphonic acid.

SUMMARY OF THE INVENTION

According to the present invention, sulfone or sulfoxide compounds can be produced industrially advantageously and with good selectivity by the reaction of a sulfide compound with hydrogen peroxide in the presence of a metal oxide described below.

The present invention provides:

1. a method for preparing a sulfone or sulfoxide compound, which comprises reacting
   a sulfide compound with hydrogen peroxide in the presence of a metal oxide catalyst obtained by reacting hydrogen peroxide with at least one metal or metal compound selected from
   a) tungsten metal,
   b) molybdenum metal,
   c) a tungsten compound comprising
      i) tungsten and
      ii) an element of a Group IIIb, IVb, Vb, or VIb excluding oxygen, and
   d) a molybdenum compound comprising
      i) molybdenum and
      ii) an element of Group IIIb, IVb, Vb, or VIb excluding oxygen.

DETAILED DESCRIPTION OF THE INVENTION

The metal oxide catalyst used in the present invention is described below.

Examples of the tungsten compound comprising tungsten and the element of group IIIb include, for example, tungsten boride.

Examples of the tungsten compound comprising tungsten and the element of Group IVb include, for example, tungsten carbide and tungsten silicide.

Examples of the tungsten compound comprising tungsten and the element of Group Vb element include, for example, tungsten nitride and tungsten phosphide.

Examples of the tungsten compound comprising tungsten and the element of Group VIb excluding oxygen include, for example, tungsten sulfide.

Examples of the molybdenum compound comprising molybdenum and the element of Group IIIb include, for example, molybdenum boride.

Examples of the molybdenum compound comprising molybdenum and the element of Group IVb include, for example, molybdenum carbide and molybdenum silicide.

Examples of the molybdenum compound comprising molybdenum and the element of Group Vb element include, for example, molybdenum nitride and molybdenum phosphide.

Examples of the molybdenum compound comprising molybdenum and the element of Group VIb excluding oxygen include, for example, molybdenum sulfide.

Preferred are tungsten metal, tungsten boride, and tungsten sulfide.

Hydrogen peroxide are generally used in a form of an aqueous solution. Alternatively, an organic solvent solution of hydrogen peroxide may be used, but aqueous hydrogen peroxide is preferred in terms of easy handling. The concentration of the aqueous hydrogen peroxide or the organic solvent solution of hydrogen peroxide is not limited, and is usually set at a concentration of 1 to 60% by weight in terms of volume efficiency and safety. Commercially available aqueous hydrogen peroxide may be used as it is, or diluted or concentrated to a desired concentration for use. The organic solvent solution of hydrogen peroxide that may be suitably used may be prepared by extracting aqueous hydrogen peroxide with the organic solvent or distilling aqueous hydrogen peroxide in the presence of the organic solvent.

Hydrogen peroxide is usually used in an amount of at least 3 moles, preferably at least 5 moles per mol of the metal or metal compound without upper limit.

The metal or metal compound is usually reacted with hydrogen peroxide in an aqueous solution. The reaction also may be conducted in an organic solvent such as an ether solvent such as diethyl ether, methyl tert-butyl ether, and tetrahydrofuran; an ester solvent such as ethyl acetate; an alcohol solvent such as methanol, ethanol, and tert-butanol; and a nitrile solvent such as acetonitrile and propionitrile, or a mixture of the organic solvent and water.

The metal or metal compound and the hydrogen peroxide are typically mixed to contact with each other, and the contacting is usually conducted by stirring in such a way that the metal or metal compound is sufficiently dispersed in the solution or susupension for preparing the metal oxide. Specifically, small particle size powder of the metal or metal compound is preferably used to enhance the contact efficiency between the metal or metal compound and the hydrogen peroxide and facilitate the controlling of the production of the metal oxide.

The metal oxide is generally prepared at a temperature of −10° C. to 100° C.

The metal or metal compound and the hydrogen peroxide are allowed to react with each other usually in water, the organic solvent, or the mixture solvent of the water and the organic solvent, in which the metal or metal compound is partially or entirely dissolved to form a homogeneous preparation solution or a suspension containing the metal oxide. The metal oxide may be extracted from the preparation solution through concentration or the like to use it as the catalyst, or the preparation solution may be used as it is.

Next, a description will be made to the process for producing the sulfone or sulfoxide compound by reacting the sulfide compound with hydrogen peroxide in the presence of the above-mentioned metal oxide.

The oxidation process of the present invention as described above can be applied to various sulfide compounds.

Examples of the sulfide compound include, for example, a sulfide compound of formula (1):

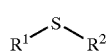
(1)

wherein $R^1$ and $R^2$ are the same or different and independently represent a substituted or unsubstituted hydrocarbyl group (e.g, a substituted or unsubstituted alkyl group, a substituted or unsubstituted alkenyl group, and a substituted or unsubstituted aryl group), or $R^1$ and $R^2$, together with the sulfur atom to which they are bonded, form a substituted or unsubstituted cyclic sulfide compound.

Examples of the sulfide compound of formula (1) include, for example, a thiophene compound of formula (2):

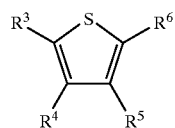
(2)

wherein $R^3$, $R^4$, $R^5$ and $R^6$ are the same or different and each independently represent a hydrogen atom,
a substituted or unsubstituted hydrocarbyl group,
a halogen atom, a nitro group, a cyano group,
a substituted or unsubstituted silyl group,
a substituted or unsubstituted imide group of formula:

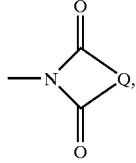

wherein Q represents a substituted or unsubstituted alkylene or arylene group, or
a group of formula: X—Y—,
wherein X represents a hydrogen atom, or
a substituted or unsubstituted hydrocarbyl group, and
Y represents —O—, —CO—, —C(O)O—, —O(O)C—, —C(O)N(Z)—, —N(Z)C(O)—, wherein Z represents a hydrogen atom or a substituted or unsubstituted hydrocarbyl group, or
two adjacent groups among $R^3$, $R^4$, $R^5$ and $R^6$ together with the thiophene ring to which they are bonded form a fused ring.

The cyclic sulfide compound of formula (2) include, for example, a dibezothiophene compound of formula (3):

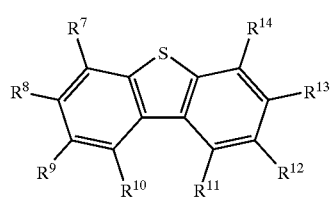
(3)

wherein $R^7$, $R^8$, $R^9$, $R^{10}$, $R^{11}$, $R^{12}$, $R^{13}$ and $R^{14}$ are the same or different and each independently represent a hydrogen atom,
a substituted or unsubstituted hydrocarbyl group,
a halogen atom, a nitro group, a cyano group,
a silyl group,
an imide group of formula:

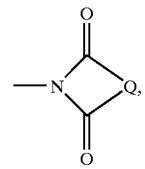

wherein Q represents a substituted or unsubstituted alkylene or arylene group, or
a group of formula: X—Y—,
wherein X represents a hydrogen atom, or
a substituted or unsubstituted hydrocarbyl group, and
Y represents —O—, —CO—, —C(O)O—, —O(O)C—, —C(O)N(Z)—, —N(Z)C(O)—, wherein Z represents a hydrogen atom or a substituted or unsubstituted hydrocarbyl group,
or two adjacent groups among $R^7$, $R^8$, $R^9$, $R^{10}$, $R^{11}$, $R^{12}$, $R^{13}$ and $R^{14}$ together with the benzene ring to which they are bonded form a fused ring (e.g., naphtho group and the like).

A description will be made to the $R^1$ to $R^{17}$ groups.

Examples of the unsubstituted hydrocarbyl group include, for example, an alkyl, alknenyl, and aryl groups and an aralkyl, arylalkenyl group.

Examples of the substituted hydrocarbyl group represented by $R^1$ to $R^{17}$, X and Z include, for example,
a hydrocarbyl group substituted with a halogen atom or atoms (e.g. fluorine, chlorine, bromine, and iodine), a nitro, cyano, or trisubstituted silyl group, an imide group of formula (a):

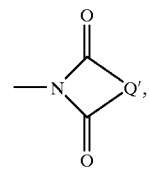
(a)

wherein Q' represents a substituted or unsubstituted alkylene (e.g. dimethylene, trimethylene and the like) or arylene group(e.g. 1,2-phenylene, 1,8-naphthylene, 2,2'-biphenylene and the like) or a group of formula: X'—Y'—,
wherein X' represents a hydrogen atom, or an unsubstituted hydrocarbyl group, and
Y' represents —O—, —CO—, —C(O)O—, —O(O)C—, —C(O)N(Z')—, —N(Z')C(O)—, wherein Z' represents a hydrogen atom or an unsubstituted hydrocarbyl group.

Examples of the group of formula: X—Y— as defined above include, for example, a substituted or unsubstituted alkoxy group,
a substituted or unsubstituted aryloxy group,
a substituted or unsubstituted aralkyloxy group,
a substituted or unsubstituted acyl group,
a substituted or unsubstituted acyloxy group,
a substituted or unsubstituted carboxy group, and
a substituted or unsubstituted amide group(e.g. acylamino or aminocarbonyl group).

Examples of the substituted or unsubstituted alkyl group include, for example, a straight or branched chain or cyclic alkyl group having 1 to 20 carbon atoms such as a methyl group, an ethyl group, a n-propyl group, an isopropyl group, a n-butyl group, an isobutyl group, a sec-butyl group, a tert-butyl group, a n-pentyl group, a n-decyl group, a cyclopropyl group, a 2,2-dimethylcyclopropyl group, a cyclopentyl group, a cyclohexyl group, a menthyl group, and alkyl groups substituted with at least one group selected from an alkoxy group (e.g. a methoxy group, an ethoxy group and the like),
an aryloxy group (e.g. a phenoxy group, and the like),
an aralkyloxy group (e.g. abenzyloxy group, and the like),
a halogen atom (e.g. fluorine and chlorine atoms),
an acyl group (e.g. an acetyl group and a benzoyl group),
an alkoxycarbonyl group (e.g. a methoxycarbonyl group and an ethoxycarbonyl group),
an aryloxycarbonyl group (e.g a phenoxycarbonyl group),
an aralkyloxycarbonyl group (e.g. a benzyloxycarbonyl group, and
a carboxyl group.

Examples of the alkoxy group include, for example, a C1–20 alkoxy group such as a methoxy group, an ethoxy group, n-proxy group, an isopropoxy group, n-butoxy group, an isobutoxy group, a sec-butoxy group, a tert-butoxy group, an n-pentyloxy group, an n-hexyloxy group, an n-heptyloxy group, an n-octyloxy group, a 2-ethylhexyloxy group, an n-nonyloxy group, an n-decyloxy group, a 3,7-dimethyloctyloxy group, a lauryloxy group, cyclopropyloxy group, 2,2-dimethylcyclopropyloxy group, a cyclopentyloxy group, a cyclohexyloxy group, a menthyloxy group, a undecyloxy, dodecyloxy, tridecyloxy, tetradecyloxy, oentadecyloxy, hexadecyloxy, heptadecyloxy, octadecyloxy, nonadecyloxy, dodecyloxy or the like.

Examples of the aryloxy group include, for example, a phenoxy group, a 1-naphthyloxy group, 2-naphthyloxy group, and the examples of the substituted aryloxy group include, for example, the aryloxy group substituted with the above-mentioned alkyl group, the above-mentioned alkoxy group, and a halogen atom.

Examples of the aryloxy group include, for example, C6–60 aryloxy group such as 4-methylphenoxy group, 4-ethylphenoxy group, 1,3,5-trimethylphenoxy group, 2-methoxyphenoxy group, and a pentafluorophenoxy group.

Examples of the aralkyloxy group, include, for example, C7–60 aralkyloxy group composed of the above-mentioned alkoxy group and the aryl groups, and specific examples thereof include, for example, a benzyloxy group, 2-phenylethoxy group, 4-phenylbutoxy group, a 5-phenylpentyloxy group, a 6-phenylhexyloxy group, a 7-phenylheptyloxy group, a 8-phenyloctyloxy group, and the like.

Examples of the halogen atom include, for example, a fluorine atom, a chlorine atom.

Examples of the acyl group include, for example, a C1–20 acyl group such as an acetyl group, a propionyl group, a butyryl group, an isobutyryl group, a pivaloyl group, a benzoyl, a trufluoroacetyl group, a pentafluorobenzoyl, and the like.

Examples of the alkoxycarbonyl group include, for example, C2–20 alkoxycarbonyl group composed of a carbonyl group and the above-mentioned alkoxy groups, and specific examples thereof include, for example, a methoxycarbonyl group and an ethoxycarbonyl group and the like.

Examples of the aryloxycarbonyl group include, for example, C7–60 aryloxycarbonyl group composed of a carbonyl group and the aryloxy group as defined above, and specific examples thereof include, for example, a phenoxycarbonyl group, and the like.

Examples of the aralkyloxycarbonyl group include, for example, C8–60 aralkyloxycarbonyl group composed of a carbonyl group and the aralkyloxy group as defined above, and specific examples thereof include, for example, a benzyloxycarbonyl group, and the like.

Examples of the substituted alkyl group include, for example, a fluoromethyl group, a chloromethyl group, a trifluoromethyl group, a pentafluoro ethyl group, a perfluoro butyl, a perfluorohexyl group, a perfluorooctyl group, a methoxy methyl group, an ethoxymethyl group, a methoxyethyl group, a methoxymethylcarbonyl group, etc.

Examples of the substituted or unsubstituted aryl group include, for example, a C6–60 aryl group such as a phenyl group, a naphthyl group, and a substituted phenyl or naphthyl group in which the aromatic ring(s) has a substituent(s) such as the above-mentioned alkyl group, an aryl group, an aralkyl group as described below, an alkoxy group, an aryloxy group, an aralkyloxy group, a halogen atom, an acyl group, an acylamino group, a nitro group, a cyano group, a carboxyl group, an alkoxycarbonyl group and the like.

Specific examples thereof include, for example, a 2-methylphenyl group, a 4-chlorophenyl group, a 4-methylphenyl group, a 4-methoxyphenyl group, a 3-phenoxyphenyl group, 2-nitrophenyl group, 4-cyanophenyl group, 3-methoxycarbonylphenyl group and the like.

Examples of the substituted or unsubstituted aralkyl group include those composed of the aryl group and the alkyl group, and specific examples thereof include, for example, a benzyl group, a 4-chlorobenzyl group, a 4-methylbenzyl group, a 4-methoxybenzyl group, a 3-phenoxybenzyl group, a 2,3,5,6-tetrafluorobenzyl group, a 2,3,5,6-tetrafluoro-4-methylbenzyl group, a 2,3,5,6-tetrafluoro-4-methoxybenzyl group, a 2,3,5,6-tetrafluoro-4-methoxymethylbenzyl group, phenethyl group, phenylbutyl group, phenylhexyl group or the like.

Examples of the substituted alkoxy group include, for example, a trifluoromethoxy group, a pentafluoroethoxy group, a par fluorobutoxy group, a perfluor hexyloxy group, a perfluorooctyloxy group, a methoxymethoxy group, 2-methoxyethoxy group, etc.

Examples of the substituted aryloxy group include, for example, 2-methylphenoxy group, 4-methylphenoxy group, 2-ethylphenoxy group, 2,4-dimethylphenoxy group, 2,4,6-trimethylphenoxy group, 2-methyl-4-ethylphenoxy group, 4-decylphenoxy group, 4-chlorophenoxy group, 4-methoxyphenoxy group, 3-phenoxyphenoxy group, 2-nitroglycerine phenoxy group, 4-cyanophenoxy group, 3-methoxycarbonylphenoxy group, pentafluorophenoxy group, and the like.

Examples of the substituted arlkyloxy group include, for example, a 4-chlorobenzyloxy group, a 4-methylbenzyloxy group, a 4-methoxybenzyloxy group, a 3-phenoxybenzyloxy group, 2,3,5,6-tetrafluorobenzyloxy group, 2,3,5,6- tetrafluoro-4-methylbenzyloxy group, 2,3,5,6-tetrafluoro-4-methoxybenzyloxy group, 2,3,5,6-tetrafluoro-4-methoxymethylbenzyloxy group, a phenylethoxy group, a phenylbutoxy group, a phenylhexyloxy group, etc.

Examples of the unsubstituted alkenyl group include, for example, a C2–12 alkenyl group such as an ethenyl group, 1-propenyl group, 2-propenyl group, 1-methylethenyl group, 1-butenyl group, 2-butenyl group, 3-butenyl group, 1-methyl-1-propenyl group, a 2-methyl-1-propenyl group, a 1-methyl-2-propenyl group, 1-pentenyl group, 2-pentenyl group, 3-pentenyl group, 1-hexenyl group, 2-cyclopentenyl group and 2-cyclohexenyl, 1-decenyl group, and the like.

Examples of the substituted alkenyl group include, for example, an alkenyl group substituted an alkoxy group, anaryloxy group, an aralkyloxy group, a halogen atom, an acyl group, a alkoxycarbonyl group, a aryoxycarbonyl group, a aralkyloxycarbonyl group, and a carboxyl group.

Specific examples of the substituted or unsubstituted alkenyl group include, for example, an arylalkenyl group such as a styryl group etc.

Examples of the silyl group substituted with 1–3 substituents selected from the substituted or unsubstituted alkyl group, a substituted or unsubstituted aryl group, and a substituted or unsubstituted aralkyl group.

Specific examples of the trisubstituted silyl group include, for example, a trimethylsilyl, a triethylsilylmethyl, a tri(n-propyl)silyl group, a triisopropylsilyl group, a dimethylisopropylsilyl group, a diethylisopropylsilyl group, a tert-butyldimethylsilyl group, a pentyldimethylsilyl group, a hexyldimethylsilyl group, a triphenylsilyl group, a tribenzylsilyl group, a diphenylmethylsilyl group, a dimethylphenylsilyl group, a tert-butyldiphenylsilyl group, etc.

Examples of the substituted or unsubstituted acyl group include, for example, groups composed of the substituted or unsubstituted alkyl, aryl, or aralkyl group and a carbonyl group such as an acetyl, propionyl, butyryl, isobutyryl, pivaloyl, benzoyl, trifluoroacetyl, pentafluorobenzoyl or the like.

Examples of the aralkylcarbonyl group include, for example, those composed of the aryl group and a carbonyl group.

Specific examples of the substituted or unsubstituted acyloxy group include, for example, an acetoxy group, a propionyloxy group, a butyryloxy group, an isobutyryloxy group, a pivaloyloxy group, a benzoyloxy group, a trifluoroacetoxy group, a pentafluorobenzoyloxy group, etc.

Examples of the substituted or unsubstituted amide group include, for example, a formamide group, an acetamide group, a propionamide group, a butyramide group, a benzamide group, a trifluoroacetamide group, a pentafluorobenzamide group, a diformamide group, a diacetamide group, a dipropionamide group, a dibutyramide group, a dibenzamide group, a ditrifluoroacetamide group, a dipentafluorobenzamide group, etc.

Examples of the substituted or unsubstituted imide groups are illustrated below. In the figure below, "•" denotes a bonding position.

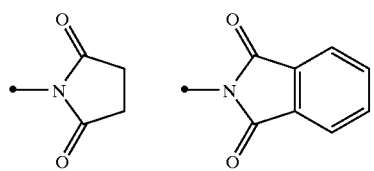

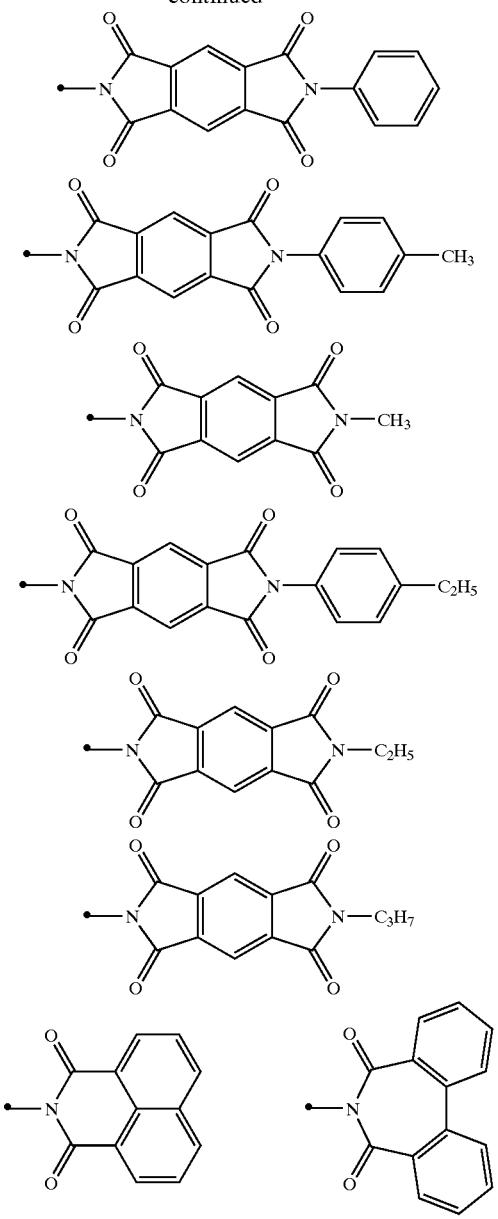

Examples of the substituted or unsubstituted carboxyl group include, for example, a substitutedcarbonyl group as alkoxycarbonyl group which may be substituted.

Specifically, a methoxycarbonyl group, an ethoxycarbonyl group, a propoxycarbonyl group, a hexyloxycarbonyl group, etc.

Examples of the sulfide compound used for this invention include, for example, dimethyl sulfide, diethyl sulfide, di(n-propyl) sulfide, di(n-butyl) sulfide, di(n-amyl) sulfide, di(n-hexyl) sulfide, di(n-heptyl) sulfide, di(n-octyl) sulfide, di(n-nonyl) sulfide, di(n-decyl) sulfide, di(n-dodecyl) sulfide, di(isopropyl) sulfide, di(isobutyl) sulfide, di(sec-butyl) sulfide, di(tert-butyl) sulfide, di(isoamyl) sulfide, methyl butyl sulfide, dicyclopentyl sulfide, dicyclohexyl sulfide, dicyclododecyl sulfide, diphenyl sulfide, dibenzyl sulfide, methyl phenyl sulfide, ethyl phenyl sulfide, di(4-chlorophenyl) sulfide, di(3-methoxyphenyl) sulfide, di(2,4-dichlorophenyl) sulfide, di(4-trifluoromethylphenyl) sulfide, di(4-nitroglycerine phenyl) sulfide, (4-fluorophenyl)

(4-tolyl) sulfide, (3-chlorophenyl) (4-tolyl) sulfide, (4-nitrophenyl) (4-chloromethylphenyl) sulfide, (2-nitrophenyl) phenyl sulfide, (4-chloromethylphenyl) phenyl sulfide, 9H-thioxanthene-9-on, 3-acetamide-9H-thioxanthene-9-on, 3-methoxycarbonyl-9H-thioxanthene-9-on, phenoxathyne, 1-ethylphenoxathyne, 3-(2-trifluoromethyethoxy)phenoxathyne, (2-hydroxyethyl) phenyl sulfide, (chloromethyl) phenyl sulfide, tetrahydrothiophene, (methoxycarbonylmethyl)benzo[b]thiophene, 3-chlorobenzo[b]thiophene, 5-methylbenzo[b]thiophene, 3,5-dibromobenzo[b]thiophene, 3,4-dichlorobenzo[b]thiophene, 4,7-dimethoxybenzo[b]thiophene, dibenzothiophene, 3-octyloxybenzo[b]thiophene, 5-octyloxybenzo[b]thiophene, 3,5-dioctyloxybenzo[b]thiophene, 3,4-dioctyloxybenzo[b]thiophene, 4,7-dioctyloxybenzo[b]thiophene, 2,3-dioctyldibenzothiophene, 2,8-dioctyldibenzothiophene, 2,3-dioctyloxydibenzothiophene, 2,8-dioctyloxydibenzothiophene, 1,9-dioctyloxydibenzothiophene, 4,6-dioctyloxydibenzothiophene, 1,2,8,9-tetraoctyloxydibenzothiophene, 1,4,6,9-tetraoctyloxydibenzothiophene, 1,2,4,6,8,9-hexaoctyloxydibenzothiophene, 1,3-dioctyloxydibenzothiophene, 1,2,9-trioctyloxydibenzothiophene, 3,4-dioctyloxydibenzothiophene, 1,2,3,4,6,9-hexaoctyloxydibenzothiophene, 2,3-dichlorodibenzothiophene, 2,8-dichlrodibenzothiophene, 2,3-difluorodibenzothiophene, 2,8-difluorodibenzothiophene, 2,3-diphenyldibenzothiophene, 2,8-diphenyldibenzothiophene, 2,3-dipehnoxydibenzothiophene, 2,8-diphenoxydibenzothiophene, 2,3-dibenzyldibenzothiophene, 2,8-dibenzyldibenzothiophene, 2,3-dibenzyloxydibenzothiophene, 2,8-dibenzyloxydibenzothiophene, 2,3-bis(trimethylsilyl)dibenzothiophene, 2,8-bis(trimethylsilyl)dibenzothiophene, 2,3-bis(triphenylsilyl)dibenzothiophene, 2,8-bis(triphenylsilyl)dibenzothiophene, 2,3-bis(tribenzylsilyl)dibenzothiophene, 2,8-bis(tribenzylsilyl)dibenzothiophene, 2,3-diacetyldibenzothiophene, 2,8-diacetyldibenzothiophene, 2,3-diacetoxybenzothiophene, 2,8-diacetoxybenzothiophene, 2,3-bis(diacetylamino)dibenzothiophene, 2,8-bis(diacetylamino)dibenzothiophene, 2,3-bis(styryl)dibenzothiophene, 2,8-bis(styryl)dibenzothiophene, 2,3-dicyanodibenzothiophene, 2,8-dicyanodibenzothiophene, dinaphtho[2,1-b: 1',2'-d]dibenzothiophene, dianthro[2,1-b: 1' 2'-d]dibenzothiophene, etc.

By the reaction of the sulfide compound with the hydrogen peroxide in the presence of the above-mentioned metal oxide catalyst, the sulfur atom of the sulfide compound is oxidized and the sulfone or sulfoxide compound is formed.

The sulfide compound of formula (1) is used to form the sulfone compound of formula (4):

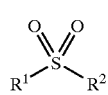

(4)

wherein $R^1$ and $R^2$ have the same meaning as defined above, or the sulfoxide compound of formula (5):

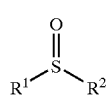

(5)

wherein $R^1$ and $R^2$ have the same meaning as defined above. The sulfoxide compound of formula (5) may also be used to produce the sulfone compound of formula (4) and the reaction is usushally conducted by reacting the sulfoxide compound of formula (5) with hydrogen peroxide in the presence of the metal oxide catalyst as used to produce the sulfone compound or sufoxide compound from the sulfide compound of formula (1). The following sulfone compound of formula (6):

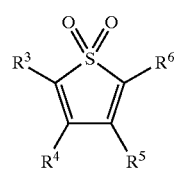

(6)

wherein $R^3$, $R^4$, $R^5$ and $R^6$ have the same meaning as defined above, or the following sulfoxide compound of formula (7):

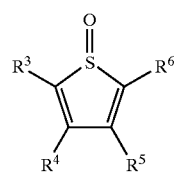

(7)

wherein $R^3$, $R^4$, $R^5$ and $R^6$ have the same meaning as defined above, is obtained by reacting the sulfide compound of formula (2) as defined above with hydrogen peroxide in the presence of the metal oxide catalyst of the present invention.

The following sulfone compound of formula (8):

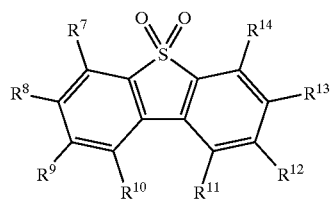

(8)

wherein $R^7$ to $R^{14}$ are the same as defined above, or the following sulfoxide compound of formula (9):

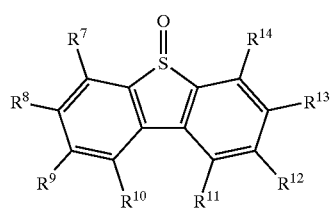

(9)

wherein $R^7$ to $R^{14}$ have the same meaning as defined above is obtained by the reaction of the sulfide compound of formula (3) above with hydrogen peroxide in the presence of the metal oxide catalyst of the present invention.

In the reaction of the sulfide compound with the hydrogen peroxide, the metal oxide is generally used in a catalytic amount, and usually in an amount of at least 0.0005 mol per mol of the sulfide compound without upper limit, but in terms of economy, an amount of one mol or less per mol of the sulfide compound is preferably used.

The hydrogen peroxide is generally used in the form of aqueous hydrogen peroxide. Of course, a hydrogen peroxide in an inert organic solvent solution may be used. The aqueous hydrogen peroxide or the organic solvent solution can contain the hydrogen peroxide at any concentration without limit, but practically at a concentration of 1 to 60% by weight in terms of volume efficiency and safety. Commercially available aqueous hydrogen peroxide may be used as it is, or diluted or concentrated to a desired concentration for use. For example, the hydrogen peroxide solution in an inert organic solvent can be prepared by extracting aqueous hydrogen peroxide with the inert organic solvent or distilling aqueous hydrogen peroxide in the presence of the inert organic solvent.

The hydrogen peroxide is generally used at least 0.8 mol per mol of the sulfide compound without upper limit. However, too much a usage may be economically disadvantageous, and 10 moles or less per mol of the sulfide compound is preferred. In the reaction, either the sulfone compound or the sulfoxide compound can selectively be produced by controlling the amount of the hydrogen peroxide. For example, the sulfone compound can selectively be produced by using the hydrogen peroxide, for example, in an amount of 1.5 moles or more per mol of the sulfide compound, and the sulfoxide compound can selectively be produced typically by using the hydrogen peroxide in an amount of at least 0.8 mol and less than 1.5 moles per mol of the sulfide compound. If the metal oxide-containing liquid preparation is used, the amount of the hydrogen peroxide in the preparation may be taken account into the amount thereof to be used.

The reaction is generally allowed to proceed in water, an organic solvent, or a mixture solvent of an organic solvent and water. Examples of the organic solvent include ether solvents such as diethyl ether, methyl tert-butyl ether, and tetrahydrofuran; ester solvents such as ethyl acetate; alcohol solvents such as methanol, ethanol, and tert-butanol; nitrile solvents such as acetonitrile and propionitrile; aromatic hydrocarbon solvents such as toluene, xylene, and chlorobenzene; and aliphatic hydrocarbon solvents such as cyclohexane and n-heptane. The amount of the water or the organic solvent that may be suitably used is not limited, but in terms of volume efficiency and the like, 100 parts by weight or less per 1 part by weight of the sulfide compound is practical.

At too low a temperature, the reaction can less proceed, and at too high a temperature, side reactions such as decomposition of the raw sulfide compound or the produced sulfone or sulfoxide compound can proceed. The reaction temperature is therefore preferably in the range of −20° C. to 100° C.

Generally, the reaction is allowed to proceed by mixing the sulfide compound, the hydrogen peroxide, and the metal oxide catalyst to bring them into contact with each other, with no limit to the order of mixing. Alternatively, the metal or metal compound, the hydrogen peroxide, and the sulfide compound may be mixed and brought into contact with each other, so that the reaction of the sulfide compound with the hydrogen peroxide is allowed to proceed while the metal oxide catalyst is prepared.

The reaction may be allowed to proceed in the presence of a phase-transfer catalyst. Examples of the phase-transfer catalyst include quaternary ammonium salts, quaternary phosphonium salts, and large-ring polyethers. The quaternary ammonium salts are preferred.

Examples of the quaternary ammonium salts include quaternary ammonium chlorides such as trioctylmethylammonium chloride, trioctylethylammonium chloride, dilauryldimethylammonium chloride, lauryltrimethylammonium chloride, stearyltrimethylammonium chloride, lauryldimethylbenzylammonium chloride, tricaprylmethylammonium chloride, tridecylmethylammonium chloride, trihexylmethylammonium chloride, tridodecylmethylammonium chloride, tetrabutylammonium chloride, benzyltrimethylammonium chloride, benzyltriethylammonium chloride, N-laurylpyridinium chloride, N-cetylpyridinium chloride, and N-laurylpicolinium chloride; quaternary ammonium bromides each having the bromide ion in place of the chloride ion in each structure of the above-mentioned quaternary ammonium chlorides; quaternary ammonium iodides each having the iodide ion in place of the chloride ion in each structure of the above-mentioned quaternary ammonium chlorides; quaternary ammonium sulfites each having the sulfite ion in place of the chloride ion in each structure of the above-mentioned quaternary ammonium chlorides; quaternary ammonium sulfates each having the sulfate ion in place of the chloride ion in each structure of the above-mentioned quaternary ammonium chlorides; and quaternary ammonium hydrogensulfates each having the hydrogensulfate ion in place of the chloride ion in each structure of the above-mentioned quaternary ammonium chlorides.

Examples of the quaternary phosphonium salts include tetrabutylphosphonium bromide, and examples of the large-ring polyethers include 12-crown-4, 18-crown-6, and benzo-18-crown-6.

The phase-transfer catalyst is generally used in an amount of 0.0005 molar times or more based on the sulfide compound without upper limit, but in terms of economy, an amount of one molar time or less based on the sulfide compound is practical. The phase-transfer catalyst may also be used in the above-mentioned preparation of the oxide metal catalyst.

The reaction may be allowed to proceed under atmospheric pressure or pressurerized pressure. The reaction process may be monitored by conventional analysis techniques such as gas chromatography, high performance liquid chromatography, thin layer chromatography, NMR, IR, and the like.

After the conclusion of the reaction, the reaction liquid, as such or optionally treated with a reducing agent such as sodium thiosulfate and sodium hydrogensulfite for decomposition of the remaining hydrogen peroxide, is subjected to such a treatment as concentration and crystallization for collecting the target sulfone or sulfoxide compound. Alternatively, the reaction liquid, as such or optionally with water and/or a water-insoluble organic solvent added, is subjected to extraction, and the resulting organic layer is concentrated to give the sulfone or sulfoxide compound. The resulting sulfone or sulfoxide compound may be purified by such a process as distillation and column chromatography.

Examples of the water-insoluble organic solvent include, for example, aromatic hydrocarbon solvents such as toluene, xylene, and chlorobenzene; halogenated hydrocarbon solvents such as dichloromethane, dichloroethane, and chloroform; ether solvents such as diethyl ether, methyl tert-butyl ether, and tetrahydrofuran; and ester solvents such as ethyl acetate. The usage thereof is not particularly restricted.

The resulting filtrate after the removal of the desired sulfone or sulfoxide compound by the crystallization process, or the resulting water layer after the extraction process of the reaction mixture contains the metal oxide catalyst, which may be usable for further reaction. The filtrate or the water layer, as such or optionally concentrated, may be used for the reaction.

Examples of the sulfone compound include, for example, dimethyl sulfone, diethyl sulfone, di(n-propyl) sulfone, di(n- butyl) sulfone, di(n-amyl) sulfone, di(n-hexyl) sulfone, di(n-heptyl) sulfone, di(n-octyl) sulfone, di(n-nonyl) sulfone, di(n-decyl) sulfone, di(n-dodecyl) sulfone, di(isopropyl) sulfone, di(isobutyl) sulfone, di(sec-butyl) sulfone, di(tert-butyl) sulfone, di(isoamyl) sulfone, methylbutyl sulfone, dicyclopentyl sulfone, dicyclohexyl sulfone, dicyclododecyl sulfone, diphenyl sulfone, dibenzyl sulfone, methylphenyl sulfone, ethylphenyl sulfone, di(4-chlorophenyl) sulfone, di(3-methoxyphenyl) sulfone, di(2,4-dichlorophenyl) sulfone, di(4-trifluoromethylphenyl) sulfone, di(4-nitrophenyl) sulfone, (4-fluorophenyl) (4-tolyl) sulfone, 3-chlorophenyl 4-tolyl sulfone, (2-nitrophenyl) phenyl sulfone, (4-nitrophenyl) (4-chlorophenyl) sulfone (4-chloromethylphenyl) phenyl sulfone 10,10-dioxo-9H-thioxanthene-9-on, 10,10-dioxo-3-acetamide-9H-thioxanthene-9-on, 10,10-dioxo-3-methoxycarbonyl-9H-thioxanthene-9-on, phenoxathyne-10,10-dioxide, 1-ethylphenoxathyne-10,10-dioxide, 3-(2-trifluoromethylethoxy)phenoxathyne-10,10-dioxide, (2-hydroxyethyl) phenyl sulfone, (chlromethyl) phenyl sulfone, (methoxycarbonylmethyl) phenyl sulfone, tetramethylene sulfone, benzo[b]thiophenesulfone, 3-chlorobenzo[b]thiophenesulfone, 3,5-dibromobenzo[b]thiophene sulfone, 3,4-dichlorobenzo[b]thiophene sulfone, 5-methylbenzo[b]thiophene sulfone, 4,7-dimethoxybenzo[b]thiophene sulfone, 3-octyloxybenzo[b]thiophene sulfone, 5-octyloxybenzo[b]thiophene sulfone, 3,5-dioctyloxybenzo[b]thiophene sulfone, 3,4-dioctyloxybeno[b]thiophene sulfone, 4,7-dioctyloxybenzo[b]thiophene sulfone dibenzothiophene-5,5-dioxide, 2,3-dioctyldibenzothiophene sulfone, 2,8-dioctyldibenzothiophene sulfone, 2,3-dioctyloxydibenzothiophene sulfone, 2,8-dioctyloxydibenzothiophene sulfone, 1,9-dioctyloxydibenzothiophene sulfone, 4,6-dioctyloxydibenzothiophene sulfone, 1,2,8,9-tetraoctyloxydibenzothiophene sulfone, 1,4,6,9-tetraoctyloxydibenzothiophene sulfone, 1,2,4,6,8,9-hexaoctyloxydibenzothiophene sulfone, 1,3-dioctyloxydibenzothiophene sulfone, 1,2,9-trioctyloxydibenzothiophene sulfone, 3,4-dioctyloxydibenzothiophene sulfone, 1,2,3,4,6,9-hexaoctyloxydibenzothiophene sulfone, 2,3-dichlrodibenzothiophene sulfone, 2,8-dichlorodibenzothiophene sulfone, 2,3-difluorodibenzothiophene sulfone, 2,8-difluorodibenzothiophene sulfone, 2,3-diphenyldibenzothiophene sulfone, 2,8-diphenyldibenzothiophene sulfone, 2,3-diphenoxydibenzothiophene sulfone, 2,8-diphenoxydibenzothiophene sulfone, 2,3-dibenzyldibenzothiophene sulfone, 2,8-dibenzyldibenzothiophene sulfone, 2,3-dibenzyloxydibenzothiophene sulfone, 2,8-dibenzyloxydibenzothiophene sulfone, 2,3-bis(trimethylsilyl)dibenzothiophene sulfone, 2,8-bis(trimethylsilyl)dibenzothiophene sulfone, 2,3-bis(triphenylsilyl)dibenzothiophene sulfone, 2,8-bis(triphenylsilyl)dibenzothiophene sulfone, 2,3-bis(tribenzylsilyl)dibenzothiophene sulfone, 2,8-bis(tribenzylsilyl)dibenzothiophene sulfone, 2,3-diacetyldibenzothiophene sulfone, 2,8-diacetyldibenzothiophene sulfone, 2,3-diacetoxydibenzothiophene sulfone, 2,8-diacetoxydibenzothiophene sulfone, 2,3-bis(diacetylamino)dibenzothiophene sulfone, 2,8-bis(diacetylamino)dibenzothiophene sulfone, 2,3-bis(styryl)dibenzothiophene sulfone, 2,8-bis(styryl)dibenzothiophene sulfone, 2,3-dicyanodibenzothiophene sulfone, 2,8-dicyanodibenzothiophene sulfone, dinaphtho[2,1-b: 1',2'-d] dibenzothiophene sulfone, and dianthro[2,1-b: 1',2'-d] dibenzothiophene sulfone Examples of the sulfoxide compound include, for example, dimethyl sulfoxide, diethyl sulfoxide, di(n-propyl) sulfoxide, di(n-butyl) sulfoxide, di(n-amyl) sulfoxide, di(n-hexyl) sulfoxide, di(n-heptyl) sulfoxide, di(n-octyl) sulfoxide, di(n-nonyl) sulfoxide, di(n-decyl) sulfoxide, di(n-dodecyl) sulfoxide, di(isopropyl) sulfoxide, di(isobutyl) sulfoxide, di(sec-butyl) sulfoxide, di(tert-butyl) sulfoxide, di(isoamyl) sulfoxide, methyl butyl sulfoxide, dicyclopentyl sulfoxide, dicyclohexyl sulfoxide, dicyclododecyl sulfoxide, diphenyl sulfoxide, dibenzyl sulfoxide, methyl phenyl sulfoxide, ethyl phenyl sulfoxide, di(4-chlorophenyl) sulfoxide, di(3-methoxyphenyl) sulfoxide, di(2,4-dichlorophenyl) sulfoxide, di(4-trifluoromethylphenyl) sulfoxide, di(4-nitrophenyl) sulfoxide, 4-fluorophenyl4-tolylsulfoxide, (3-chlorophenyl) (4-tolyl) sulfoxide, (4-nitrophenyl) (4-chlorophenyl) sulfoxide, (2-nitrophenyl) phenyl sulfoxide, (4-chloromethylphenyl) phenyl sulfoxide 10-oxo-9H-thioxanthene-9-on, 10-oxo-3-acetamide-9H-thioxanthene-9-on, 10-oxo-3-methoxycarbonyl-9H-thioxanthene-9-on, phenoxathyne-10-oxide, 1-ethylphenoxathyne-10-oxide, 3-(2-trifluoromethylethoxy)phenoxthyne-10-oxide, phenyl (chloromethyl) sulfoxide, (2-hydroxyethyl) phenyl sulfoxide, tetramethylene sulfoxide, (methoxycarbonylmethyl) benzo[b]thiophene sulfoxide, 3-chlorobenzo[b]thiophene sulfoxide, 3,5-dibromobenzo[b]thiophene sulfoxide, 3,4-dichlrobenzo[b]thiophenesulfoxide, 5-methylbenzo[b]thiophene sulfoxide, 4,7-dimethoxybenzo[b]thiophene sulfoxide, 3-octyloxybenzo[b]thiophene sulfoxide, 5-octyloxybenzo[b]thiophene sulfoxide, 3,5-dioctyloxybenzo[b]thiophene sulfoxide, 3,4-dioctyloxybenzo[b]thiophene sulfoxide, 4,7-dioctyloxybenzo[b]thiophene sulfoxide dibenzothiophene-5-oxide, 2,3-dioctyldibenzothiophene sulfoxide, 2,8-dioctyldibenzothiophene sulfoxide, 2,3-dioctyloxydibenzothiophene sulfoxide, 2,8-dioctyloxydibenzothiophene sulfoxide, 1,9-dioctyloxydibenzothiophene sulfoxide, 4,6-dioctyloxydibenzothiophene sulfoxide, 1,2,8,9-tetraoctyloxydibenzothiophene sulfoxide, 1,4,6,9-tetraoctyloxydibenzothiophene sulfoxide, 1,2,4,6,8,9-hexaoctyloxydibenzothiophene sulfoxide, 1,3-dioctyloxydibenzothiophene sulfoxide, 1,2,9-trioctyloxydibenzothiophene sulfoxide, 3,4-dioctyloxydibenzothiophene sulfoxide, 1,2,3,4,6,9-hexaoctyloxydibenzothiophene sulfoxide, 2,3-dichlorodibenzothiophene sulfoxide, 2,8-dichlrodibenzothiophene sulfoxide, 2,3-diflurodibenzothiophene sulfoxide, 2,8-diflurodibenzothiophene sulfoxide, 2,3-diphenyldibenzothiophene sulfoxide, 2,8-diphenyldibenzothiophene sulfoxide, 2,3-diphenoxydibenzothiophene sulfoxide, 2,3-diphenoxydibenzothiophene sulfoxide, 2,8-dibenzyldibenzothiophene sulfoxide, 2,3-dibenzyldibenzothiophene sulfoxide, 2,8-dibenzyloxydibenzothiophene sulfoxide, 2,3-bis(trimethylsilyl)dibenzothiophene sulfoxide, 2,8-bis(trimethylsilyl)dibenzothiophene sulfoxide, 2,3-bis(triphenylsilyl)dibenzothiophene sulfoxide, 2,8-bis(triphenylsilyl)dibenzothiophene sulfoxide, 2,3-bis(tribenzylsilyl)dibenzothiophene sulfoxide, 2,8-bis(tribenzylsily)dibenzothiophene sulfoxide, 2,3- diacetyidibenzothiophene sulfoxide, 2,8-diacetyldibenzothiophenesulfoxide, 2,3-diacetoxydibenzothiophene sulfoxide, 2,8-diacetoxydibenzothiophene sulfoxide, 2,3-bis(diacetylamino)dibenzothiophene sulfoxide, 2,8-bis(diacetylamino)dibenzothiophene sulfoxide, 2,3-bis(styryl) dibenzothiophene sulfoxide, 2,8-bis(styryl) dibenzothiophene sulfoxide, 2,3-dicyanodibenzothiophene sulfoxide, 2,8-dicyanodibenzothiophene sulfoxide, dinaphtho[2,1-b:1',2'-d]dibenzothiophene sulfoxide, dianthro[2,1-b:1',2'-d]dibenzothiophene sulfoxide, etc.

The present invention is further described in detail in the following examples but not limited to them.

EXAMPLE 1

0.55 g of tungsten metal was added to 2.6 ml of water under nitrogen atmosphere, and stirred at the room temperature, 5 g of 30 wt % hydrogen peroxide was added and stirred, and aqueous solution of tungsten oxide catalyst was prepared. The aqueous solution was kept at 40° C., and 1280 ml of ethanol, and 44 g of 2,8-dioctyloxydibenzothiophene were added thereto. 25 g of 30 wt % hydrogen peroxide was added, and and reacted at 45° C. for 5 hours. Then, it was cooled with ice, 1300 ml of 6 wt % of aqueous sodium thiosulfate solution were added thereto, and toluene was added, and extracted. After washing the obtained organic layer with water, the organic phase was concentrated to give 47 g of 2,8-dioctyloxydibenzothiophene sulfone.

Yield: 99%.

EXAMPLE 2

To a 50-ml schlenk tube purged with nitrogen were added 8.0 mg of tungsten, 20.6 mg of methyltrioctylammonium hydrogensulfate and 6.1 g of 30 wt % aqueous hydrogen peroxide at room temperature. The mixture was stirred at 27° C. for 30 minutes to form an aqueous solution of tungsten oxide catalyst. To the aqueous solution, 4 g of diphenyl sulfide was added dropwise over 10 minutes and reacted under stirring at 27° C. for two hours. In the course of the reaction process, solid diphenyl sulfone was produced and precipitated to prevent stirring, and therefore 5 ml of ethyl acetate was added and the reaction was continued. After completion of the reaction, 11.3 g of 10 wt % aqueous solution of sodium hydrogensulfite was added to the reaction liquid and stirred for 30 minutes, and then 50 ml of ethylacetate and n-decane (an internal standard substance for analysis) were added, stirred and settled. The separated organic layer was analyzed by gas chromatography.

Yield of Diphenyl sulfone: 94.5% (Based on Diphenyl sulfide)

Yield of Diphenyl sulfoxide: 5.4% (Based on Diphenyl sulfide)

EXAMPLE 3

To a 50-ml schlenk tube purged with nitrogen were added 7.3 mg of tungsten and 5.6 g of 30 wt % aqueous hydrogen peroxide at room temperature. The mixture was stirred at 27° C. for 20 minutes to give an aqueous solution of a tungsten oxide catalyst. To the aqueous solution, 14.3 mg of methyltrioctylammonium chloride was added and then 3.7 g of diphenyl sulfide was added dropwise over 10 minutes and reacted under stirring at 27° C. for two hours. After completion of the reaction, 20 ml of ethyl acetate and 10.3 g of 10 wt % aqueous solution of sodium hydrogensulfite were added and stirred for 30 minutes, and then n-decane (an internal standard substance for analysis) was added, stirred and settled. The separated organic layer was analyzed by gas chromatography.

Yield of Diphenyl sulfone: 96.8% (Based on Diphenyl sulfide)

Yield of Diphenyl sulfoxide: 3.1% (Based on Diphenyl sulfide)

EXAMPLE 4

To a 50-ml schlenk tube purged with nitrogen were added 11 mg of tungsten and 100 mg of 30 wt % aqueous hydrogen peroxide at room temperature. The mixture was stirred at 40° C. for 20 minutes to form an aqueous solution of a tungsten oxide catalyst. To the aqueous solution, 3 g of ethanol and 372 mg of diphenyl sulfide were added, and then 500 mg of 30 wt % aqueous hydrogen peroxide was added dropwise over 10 minute and reacted under stirring at 40° C. for two hours. After completion of the reaction, 20 ml of ethyl acetate and n-decane (an internal standard substance for analysis) were added and stirred. The resulting solution was analyzed by gas chromatography.

Yield of Diphenyl sulfone: 99.0% (Based on Diphenyl sulfide)

Yield of Diphenyl sulfoxide: 1.0% (Based on Diphenyl sulfide)

EXAMPLE 5

To a 50-ml Schlenk tube purged with nitrogen were added 7.8 mg of tungsten metal and 2.6 g of 30 wt % aqueous hydrogen peroxide at room temperature. The mixture was stirred at 27° C. for 20 minutes to form an aqueous solution of a tungsten oxide catalyst. To the aqueous solution, 7 g of methanol and 3.9 g of diphenyl sulfide were added dropwise over 10 minutes and reacted under stirring at 27° C. for two hours. After completion of the reaction, 20 ml of ethyl acetate and 10.3 g of 10 wt % aqueous solution of sodium hydrogensulfite were added and stirred for 30 minutes, and then n-decane (an internal standard substance for analysis) was added, stirred and settled. The separated organic layer was analyzed by gas chromatography.

Yield of Diphenyl sulfone: 18.8% (Based on Diphenyl sulfide)

Yield of Diphenyl sulfoxide: 80.6% (Based on Diphenyl sulfide)

EXAMPLE 6

To a 50 mL Schlenk tube purged with nitrogen were added 11 mg of tungsten and 100 mg of 30 wt % hydrogen peroxide at room temperature, and stirred at 40° C. for 20 minutes to prepare aqueous solution of the tungsten oxide catalyst. 3 g of methanol and benzo[b]thiophene 268 mg are added, and 500 mg of 30 wt % hydrogen peroxide water were added over 10 minutes, and reacted-to give an aqueous solution at 40° C. for 2 hours. After completion of the reaction, 20 ml of ethyl acetate and n-decane (analysis business internal-standard substance) were added thereto and stirred and settled. The organic phase was analyzed by gas chromatography.

Benzo[b]thiophene sulfone yield: 99.5% ((benzo[b]thiophene basis).

Benzo[b]thiophene sulfoxide yield: 0.5% ((benzo[b]thiophene basis).

EXAMPLE 7

The reaction was carried out in a similar manner as in Example 4, except that 15 mg of tungsten sulfide were used in place of 11 mg of tungsten, and methanol was used in place of ethanol. Diphenyl sulfone yield: 99.5% (diphenyl sulfide basis). Diphenyl sulfoxide yield: 0.5% (diphenyl sulfide basis)

EXAMPLE 8

The reaction was carried out in a similar manner as in Example 4, except that 12 mg of tungsten boride were used in place of 11 mg of tungsten, and methanol was used in place of ethanol.

Diphenyl sulfone yield: 69.0% (diphenyl sulfide basis).
Diphenyl sulfoxide yield: 31.0% (diphenyl sulfide basis).

EXAMPLE 9

The reaction was carried out in a similar manner as in Example 4, except that 6 mg of molybdenum were used in place of 11 mg of tungsten, and methanol was used in place of ethanol.

Diphenyl sulfone yield: 89.0% (diphenyl sulfide basis).
Diphenyl sulfoxide yield: 11.0% (diphenyl sulfide basis).

According to the present invention, the sulfone or sulfoxide compound can be readily and selectively prepared.

What is claimed is:

1. A method for preparing a sulfone compound, which consists of reacting
    a sulfide compound with hydrogen peroxide in the presence of
        a metal oxide catalyst obtained by reacting hydrogen peroxide with at least one metal or metal compound selected from the aroup consisting of
        a) tungsten metal,
        b) molybdenum metal,
        c) a tungsten compound comprising
            i) tungsten and
            ii) an element of a Group IVb, Vb, or VIb excluding oxygen, and
        d) a molybdenum compound comprising
            iii) molybdenum and
            iv) an element of Group IVb, Vb, or VIb, excluding oxygen, and optionally a phase-transfer catalyst.

2. The method according to claim 1, wherein the sulfide compound is a sulfide compound of formula (1):

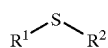
(1)

wherein $R^1$ and $R^2$ are the same or different and independently represent
    a substituted or unsubstituted hydrocarbyl group, or $R^1$ and $R^2$, together with the sulfur atom to which they are bonded, form a substituted or unsubstituted cyclic sulfide compound, and the sulfone compound is a sulfone compound of formula (4):

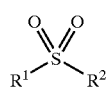
(4)

wherein $R^1$ and $R^2$ have the same meaning as defined above.

3. A method according to claim 1, wherein the sulfide compound is a sulfide compound of formula (2):

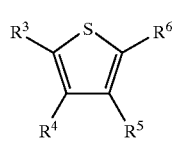
(2)

wherein $R^3$, $R^4$, $R^5$ and $R^6$ are the same or different and each independently represent a hydrogen atom,
    a substituted or unsubstituted hydrocarbyl group,
    a halogen atom, a nitro group, a cyano group,
    a substituted or unsubstituted silyl group,
    a substituted or unsubstituted imide group of formula:

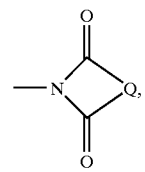

wherein Q represents a substituted or unsubstituted alkylene or arylene group, or
    a group of formula: X—Y—,
    wherein X represents a hydrogen atom, or a substituted or unsubstituted hydrocarbyl group, and
    Y represents —O—, —GO—, —C(Q)O—, —O(O)C—, —C(O)N(Z)—, —N(Z)C(O)—, wherein Z represents a hydrogen atom or a substituted or unsubstituted hydrocarbyl group,
    or two adjacent groups among $R^3$, $R^4$, $R^5$, and $R^6$ together with the thiophene ring to which they are bonded form a fused ring, and
the sulfone compound is a sulfone compound of formula (6):

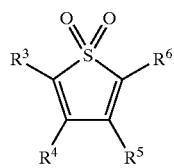
(6)

wherein $R^3$, $R^4$, $R^5$ and $R^6$ have the same meaning as defined above.

4. A method according to claim 3, wherein the cyclic sulfide compound is a sulfide compound of formula (3):

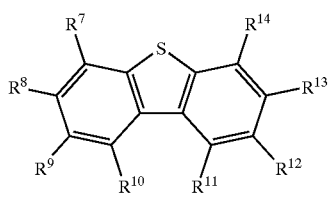
(3)

wherein $R^7$, $R^8$, $R^9$, $R^{10}$, $R^{11}$, $R^{12}$, $R^{13}$ and $R^{14}$ are the same or different and each independently represent a hydrogen atom,
    a substituted or unsubstituted hydrocarbyl group,
    a halogen atom, a nitro group, a cyano group,
    a trisubstituced silyl group, an imide group of formula:

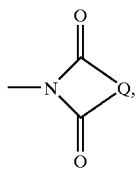

wherein Q represents a substituted or unsubstituted alkylene or arylene group, or a group of formula: X—Y—, wherein X represents a hydrogen atom, or
a substituted or unsubstituted hydrocarbyl group, and
Y represents —O—, —CO—, —C(O)O—, —O(O)C—, —C(O)N(Z)—, —N(Z)C(O)—, wherein Z represents a hydrogen atom or a substituted or unsubstituted hydrocarbyl group,
or two adjacent groups among $R^7$, $R^8$, $R^9$, $R^{10}$, $R^{11}$, $R^{12}$, $R^{13}$ and $R^{14}$ together with the benzene ring to which they are bonded form a fused ring, and
the sulfone compound is a sulfone compound of formula (8):

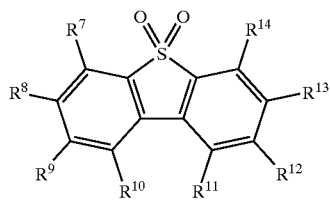

(8)

wherein $R^7$ to $R^{14}$ are the same as defined above.

5. A method for preparing a sulfone compound according to claim 1, wherein the group IVb element is carbon.

6. A method for preparing a sulfone compound according to claim 1, wherein the group Vb element is nitrogen or phosphorus.

7. A method for preparing a sulfone compound according to claim 1, wherein the VIb element exclusive of oxygen is sulfur.

8. A method for preparing a sulfone compound according to claim 1, wherein the hydrogen peroxide is an aqueous hydrogen peroxide.

9. A method for preparing a sulfone compound, which consists of reacting a sulfide compound with hydrogen peroxide in the presence of a metal oxide catalyst obtained by reacting hydrogen peroxide with at least one metal or metal compound selected from the aroup consisting of
a) tungsten metal,
b) molybdenum metal,
c) a tungsten compound comprising
  i) tungsten and
  ii) an element of a Group IVb, Vb, or VIb excluding oxygen, and
d) a molybdenum compound comprising
  i) molybdenum, and
  ii) an element of Group IVb, Vb, or VIb excluding oxygen, and optionally a phase-transfer catalyst,
wherein the hydrogen peroxide is used in an amount of at least 1.5 moles per mol of the sulfide compound.

10. A method for preparing a sufone compound, which consists of reacting a sulfoxide compound with hydrogen peroxide in the presence of the metal oxide catalyst as defined in claim 1.

* * * * *